(12) United States Patent
Bancroft et al.

(10) Patent No.: US 10,010,244 B2
(45) Date of Patent: Jul. 3, 2018

(54) HOLDER DEVICE FOR ENDOSCOPY MONITORING APPARATUS AND METHOD OF USE THEREOF

(71) Applicant: ALBERT BROWNE LIMITED, Leicester (GB)

(72) Inventors: Richard Bancroft, Leicester (GB); Martin Owen, Leicester (GB)

(73) Assignee: ALBERT BROWNE LIMITED, Leicester (GB)

( * ) Notice: Subject to any disclaimer, the term of this patent is extended or adjusted under 35 U.S.C. 154(b) by 154 days.

(21) Appl. No.: 15/022,057

(22) PCT Filed: Sep. 11, 2014

(86) PCT No.: PCT/GB2014/052753
§ 371 (c)(1),
(2) Date: Mar. 15, 2016

(87) PCT Pub. No.: WO2015/036760
PCT Pub. Date: Mar. 19, 2015

(65) Prior Publication Data
US 2016/0220098 A1   Aug. 4, 2016

(30) Foreign Application Priority Data

Sep. 16, 2013  (GB) .................................. 1316421.5

(51) Int. Cl.
*A61B 1/00*   (2006.01)
*A61B 1/12*   (2006.01)
(Continued)

(52) U.S. Cl.
CPC ............ *A61B 1/00147* (2013.01); *A61B 1/12* (2013.01); *A61B 90/70* (2016.02); *A61L 2/28* (2013.01);
(Continued)

(58) Field of Classification Search
CPC ..... A61L 12/28; A61L 2202/24; A61B 90/70; A61B 1/12; A61B 1/00147; A61B 1/0121; A61B 1/122; A61B 1/123; A61B 1/125

See application file for complete search history.

(56) References Cited

U.S. PATENT DOCUMENTS 1,437,596 A   12/1922   Korb
4,748,007 A   5/1988    Gaudion et al.
(Continued)

FOREIGN PATENT DOCUMENTS

EP   1 698 354 A1   9/2006   ............... A61L 2/28
EP   1698354 A1    9/2006
(Continued)

OTHER PUBLICATIONS

Office Action issued in corresponding Canadian Patent Application No. 2,924,740 dated Jan. 10, 2017.
(Continued)

*Primary Examiner* — Timothy J Neal
(74) *Attorney, Agent, or Firm* — Kusner & Jaffe; Michael A. Centanni

(57) ABSTRACT

A holder device is provided for use with endoscopy monitoring apparatus. The holder device includes a body portion with two or more apertures defined in said body portion. The apertures are a spaced distance apart and of such size and dimensions for the location of at least part of an indicator holding means and/or endoscopy monitoring apparatus therewith or therethrough in use.

32 Claims, 5 Drawing Sheets

(51) Int. Cl.
    *A61L 2/28*    (2006.01)
    *A61B 90/70*    (2016.01)

(52) U.S. Cl.
    CPC ..... *A61B 2090/701* (2016.02); *A61L 2202/24* (2013.01)

(56) References Cited

U.S. PATENT DOCUMENTS

| | | | |
|---|---|---|---|
| D624,658 S * | 9/2010 | Van Dalen | D24/217 |
| 2009/0081767 A1 * | 3/2009 | Ogawa | A61L 2/28 435/287.4 |

FOREIGN PATENT DOCUMENTS

| | | | | |
|---|---|---|---|---|
| EP | 1 754 449 A2 | 2/2007 | ............ | A61B 19/00 |
| EP | 1754449 A2 | 2/2007 | | |
| EP | 1886622 A1 | 2/2008 | | |
| JP | 2012-065904 A | 4/2012 | ............ | A61B 1/00 |
| JP | 2012065904 A | 4/2012 | | |
| WO | WO 2015/036760 A1 | 3/2015 | ............ | A61B 1/12 |

OTHER PUBLICATIONS

Albert Browne Limited, "International Search Report and Written Opinion", Application No. PCT/GB2014/052753, filed Sep. 11, 2014, dated Mar. 31, 2016, 11 pages.

\* cited by examiner

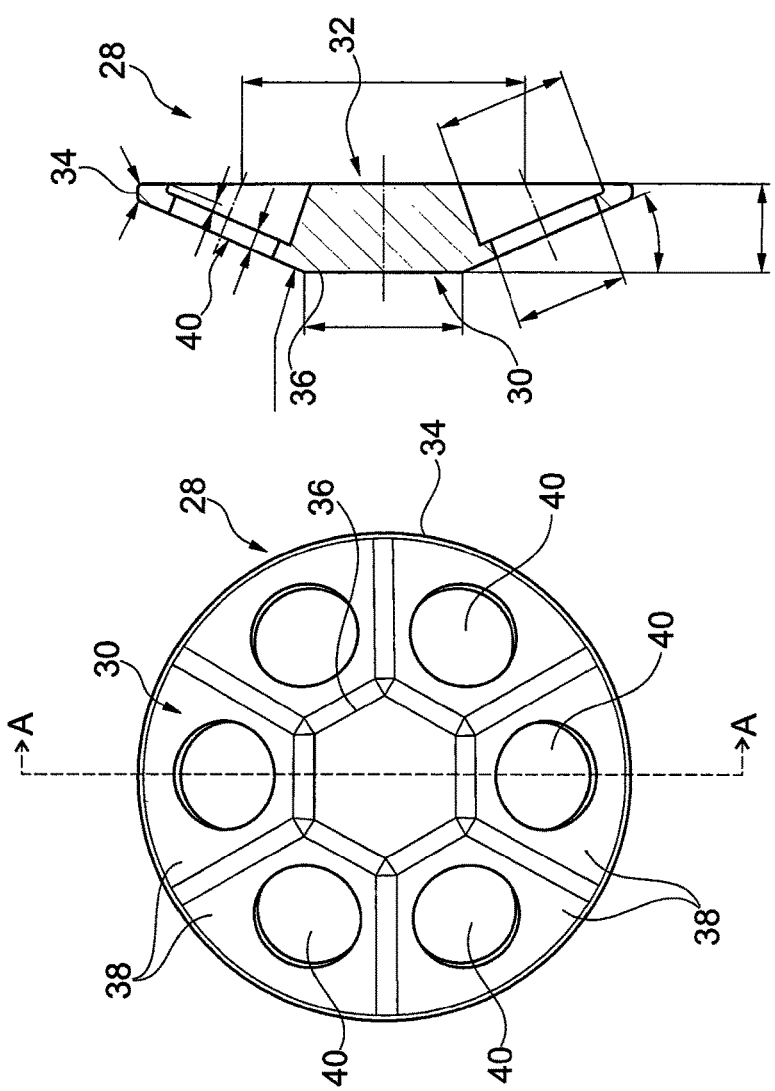
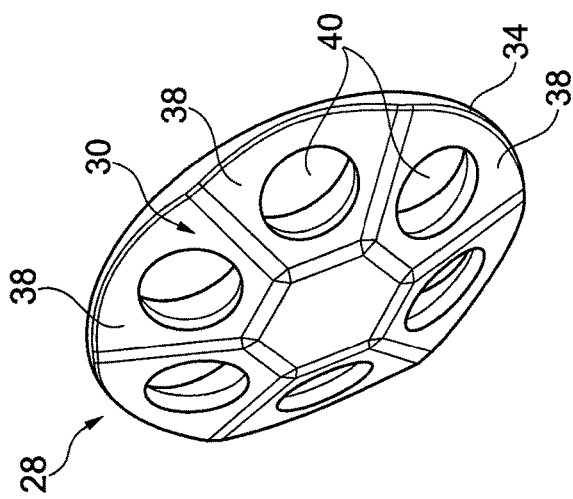
Fig. 1a  Fig. 1b  Fig. 1c

HOLDER DEVICE FOR ENDOSCOPY MONITORING APPARATUS AND METHOD OF USE THEREOF

RELATED APPLICATIONS

This application is a National Stage of International Application No. PCT/GB2014/052753 filed Sep. 11, 2014, which claims the benefit of United Kingdom Patent Application No. 1316421.5 filed Sep. 16, 2013.

This invention relates to a holder device for endoscopy monitoring and/or cleaning apparatus and to a method of use thereof.

Although the following description refers almost exclusively to a holder device for endoscopy sterilising/cleaning and/or monitoring apparatus, it will be appreciated by persons skilled in the art that the holder device could be used for holding any apparatus for any suitable purpose.

The complexity and temperature sensitivity of flexible endoscopes makes cleaning followed by sterilisation/disinfection difficult. It is therefore important that the efficacy of the cleaning, sterilisation and/or disinfection process is closely monitored. An example of a known endoscopy monitoring device comprises three elongated flexible lumen devices having a fine lumen to represent a difficult cleaning challenge. One end of each lumen device is provided with an input aperture and the opposite end of each lumen device is fitted with an indicator capsule that is used to contain a washing efficacy indicator device, such as a test soil strip, in use. Cleaning fluid is able to pass from each lumen device into the indicator capsule. The monitoring device is placed through the cleaning process and the cleaning efficacy of the process is assessed based on how clean the test soil strip is at the end of the process. Disadvantages associated with this known endoscopy monitoring device is that although the three lumen devices may be tied together using cable ties to prevent the devices from becoming separated, the indicator capsules are loose and are simply laid on an available surface during the cleaning process. The indicator capsules are therefore not provided in any reproducible orientation for each cleaning process and can be difficult to access. Furthermore, the indicator capsules are typically non-transparent and therefore a user cannot quickly and easily visually assess a test soil device located in the indicator capsule.

It is therefore an aim of the present invention to provide a holder device for overcoming the abovementioned problems.

It is a further aim of the present invention to provide a method of using a holder device.

It is a yet further aim of the present invention to provide endoscopy monitoring apparatus including a holder device.

It is a yet further aim of the present invention to provide a method of using endoscopy monitoring apparatus including a holder device.

According to a first aspect of the present invention there is provided a holder device for use with endoscopy monitoring apparatus, said holder device including a body portion with two or more apertures defined in said body portion, said apertures being a spaced distance apart and being of such size and dimensions for the location of at least part of an indicator holding means and/or endoscopy monitoring apparatus therewith or therethrough in use.

The provision of the holder device allows the indicator holding means and/or a part of endoscopy monitoring apparatus to be maintained in a user selected, fixed and/or reproducible position and/or orientation during use, to allow easy user access to the same and to allow quick and easy user visualisation of the same.

Preferably the holder device and/or body portion has at least a top or outer surface and a base or inner surface.

In one embodiment the body portion or at least part of the top or outer surface has a narrowing taper from a base edge to a top edge or point, thereby providing one or more angled surfaces, and preferably acute angled surfaces.

In one embodiment the top or outer surface is arranged to be at a substantially acute angle with respect to a horizontal axis, dome shaped, convexed in shape and/or curved in shape.

In one embodiment the body portion has a top or outer surface and a base edge on which the device is supported on a surface in use, the top or outer surface being at an acute angle with respect to the base edge or surface on which the device is supported on in use.

The angled surface or parts of the angled surface can be substantially curved and/or substantially flat.

Preferably the two or more apertures are defined in the top or outer surface, the tapered surface, the angled surface, the curved surface, convexed surface, domed surface and/or the like.

Preferably the two or more apertures pass through the holder device from the top or outer surface to the inner or base surface.

Preferably the angle of the top or outer surface in which the apertures are defined allows positioning of the indicator holding means or two or more indicator holding means at different angles and/or orientations with respect to each other, thereby allowing easy user visualisation of the same. In addition, it allows the size of the holder device to be smaller than if a linear surface were provided.

Preferably the top or outer surface, the tapered surface, angled surface, curved surface, domed surface, convexed surface and/or the like is split or divided into a number of different segments, each segment provided in a non-linear arrangement, non-planar arrangement, at a different angle and/or orientation to an adjacent segment or other segment.

Preferably the top or outer surface is divided into six different segments.

Preferably an edge defines each different segment, the walls of the body portion surface either side of the edge being provided at an angle or being non-planar with each other.

Preferably an aperture is defined in each or two or more segments and/or each segment. This allows two or more indicator holding means or endoscopy monitoring apparatus to be located at different angles and/or orientations with respect to each other, thereby allowing easy user visualisation of the same.

In one embodiment a single aperture is defined in a or each segment of the top or outer surface.

Preferably the acute angle of the top or outer surface relative to a base edge or surface on which the device is supported on in use is less than or substantially less than 90 degrees. Further preferably the acute angle is less than or equal to 45 degrees. Yet further preferably the acute angle is between 15-25 degrees, and yet further preferably is 21 degrees+/−1 degree.

In one embodiment the holder device, body portion or top or outer surface has a substantially circular base or circumferential edge to allow the device to be placed in any suitable orientation and/or position in use. However, it will be appreciated that the base edge, peripheral or circumferential edge could be any suitable shape, such as triangular, hexagonal, octagonal, pentagonal, square, rectangular and/or the like.

In one embodiment the body portion is substantially symmetrical in form but it could be asymmetrical in form.

In one embodiment the base or inner surface of the body portion is at least partially recessed, concave, curved or angled in shape.

In one embodiment the base or inner surface of the body portion is substantially solid, linear or planar in form.

Preferably the holder device is formed from any or any combination of material that can withstand a cleaning process, such as for example an endoscopy cleaning process. For example, the holder device could be formed from plastic, metal and/or the like.

In a preferred embodiment the holder device has two or more apertures, and further preferably has six or more apertures, for the location of two or more, and preferably six or more indicator holding devices and/or parts of endoscopy monitoring apparatus. The number of apertures typically corresponds to the number of endoscopy monitoring apparatus elements that need to be connected to the same in use.

According to one aspect of the present invention there is provided endoscopy monitoring apparatus including holding device.

The holding device or the endoscopy monitoring apparatus preferably includes, is associated with and/or integrally formed with two or more elongate lumen devices.

Preferably the two or more elongate lumen devices are substantially flexible in form.

Preferably a channel defined through each of said lumen devices is relatively fine to provide a relatively difficult challenge for a cleaning process to replicate the cleaning challenge that may be present with some endoscopy apparatus. For example, a diameter of the channel could be approximately between 1 mm-2 mm and/or the like.

Preferably the elongate lumen device has a longitudinal axis. Preferably a longitudinal axis of the channel is co-axial or substantially parallel to the longitudinal axis of the lumen device.

Preferably a first end of one or more elongate lumen devices has an opening through which cleaning fluid is able to pass during a cleaning process in use.

In one embodiment a second end of one or more lumen devices is provided with, associated with or integrally formed with indicator holding means or devices. Alternatively, or in addition, a second end of one or more lumen devices is provided with, or is associated with attachment means for allowing attachment to one or more indicator holding means devices and/or the holder device in use.

In one embodiment attachment means are provided on or associated with one or more indicator holding means or devices to allow attachment to a second end of one or more lumen devices.

The attachment means provided on or associated with one or more lumen devices and/or indicator holding devices can include any or any combination of one or more screw threads, nuts, bolts, clips, inter-engaging members, detachable attachment means, friction fit and/or the like.

In one embodiment the indicator holding devices are of such size, shape and/or dimensions to allow indicator means to be located therein. The indicator means are provided to allow the cleaning efficacy of a cleaning process to be assessed. In one example the indicator means is in the form of a test soil strip or device.

The test soil strip or device is typically a sheet like member on which a test soil is provided. The test soil is of such a colour that when removed, or at least partially removed, as a result of a cleaning process, user visualisation of the same is possible.

Preferably at least part of the indicator holding device is formed from substantially transparent material so that visualisation of the indicator means located therein can take place without removing the indicator means from the indicator holding device.

Removal and/or insertion of indicator means in the indicator holding device typically takes place via attachment and/or detachment of the attachment means provided on or associated with the indicator holding device, holder device and/or elongate lumen device.

Thus, in one embodiment the indicator holding device, the holding device and/or elongate lumen device are detachably attached to each other.

Preferably the second end of each lumen device is inserted into or positioned relative to a holder aperture via a base or inner surface of the holder device.

Preferably at least part of the indicator holding device protrudes outwardly from the top or outer surface of the holder device in use.

Preferably the indicator holding device is substantially rigid in form to allow the same to protrude outwardly from the holder device.

In one embodiment an attachment nut for the indicator holding device is located adjacent the top or outer surface of the holder device.

In one embodiment a second end of the elongate lumen device is provided with threaded attachment means which are locatable through one of the apertures in the holding device in use, a complementary threaded attachment nut is joined to the threaded lumen attachment means via a top or outer surface of the holding device to retain the lumen with respect to the holding device in use.

According to further independent aspects of the present invention there is provided a method of using a holder device and a method of using endoscopy monitoring apparatus.

According to an aspect of the present invention there is provided a method of using a holder device, holder device for use with endoscopy monitoring apparatus, said holder device including a body portion with two or more apertures defined in said body portion, said apertures being a spaced distance apart and said method including the step of locating at least part of an indicator holding means and/or endoscopy monitoring apparatus therewith or therethrough in use.

An embodiment of the present invention will now be described with reference to the accompanying figures, wherein:

FIGS. 1a-1c show a plan view from above, a cross sectional view taken along line A-A in the plan view, and a perspective view of a holder device according to an embodiment of the present invention respectively;

Figure 2:
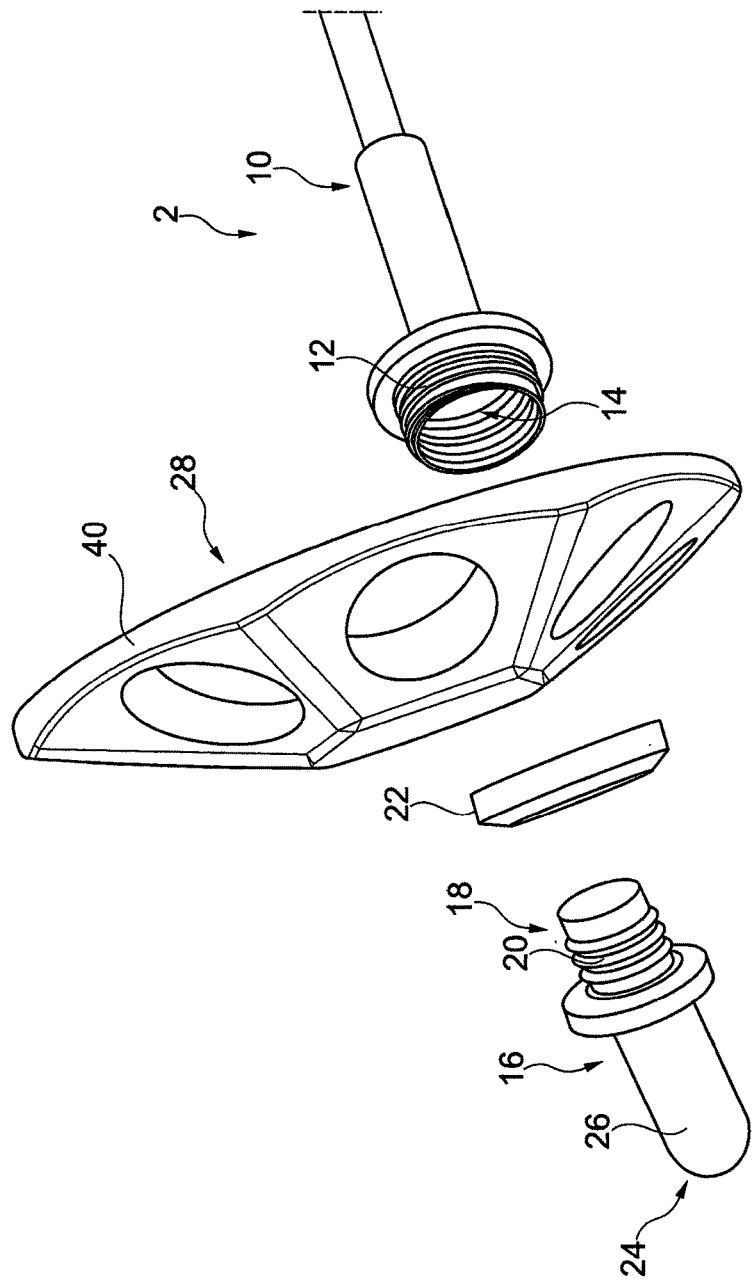
FIG. 2 is an exploded view of an indicator holding device, holder device and elongate lumen according to an embodiment of the present invention.
Figure 3:
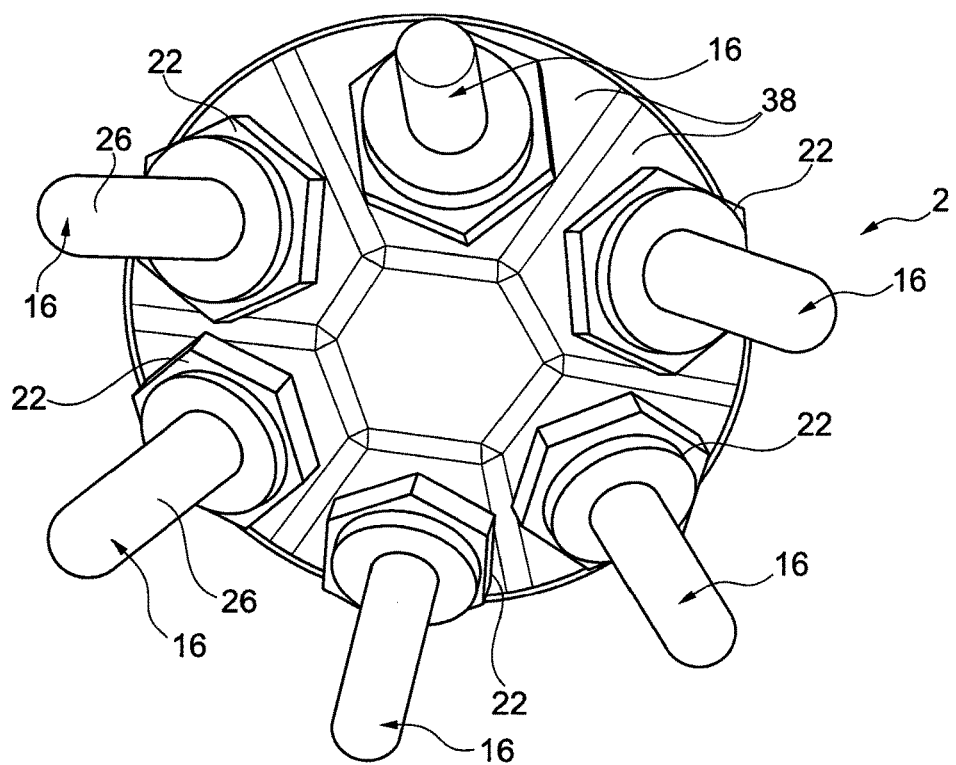
FIG. 3 is an end view of the endoscopy monitoring apparatus.
Figure 4:
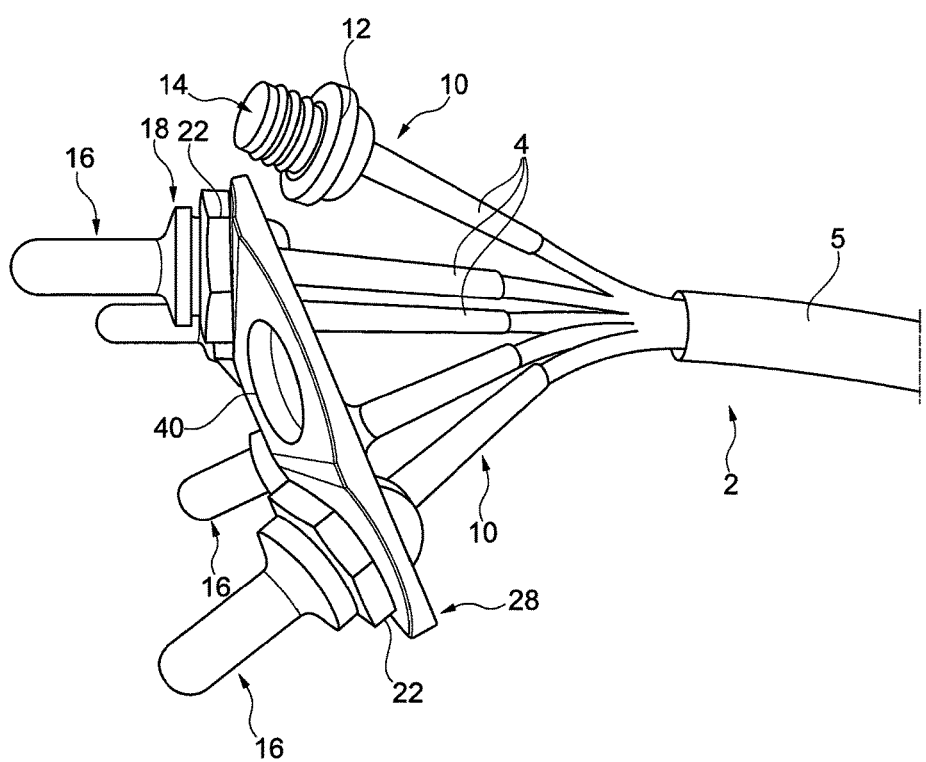
FIG. 4 is a side view of the end of the endoscopy monitoring apparatus.
Figure 5:
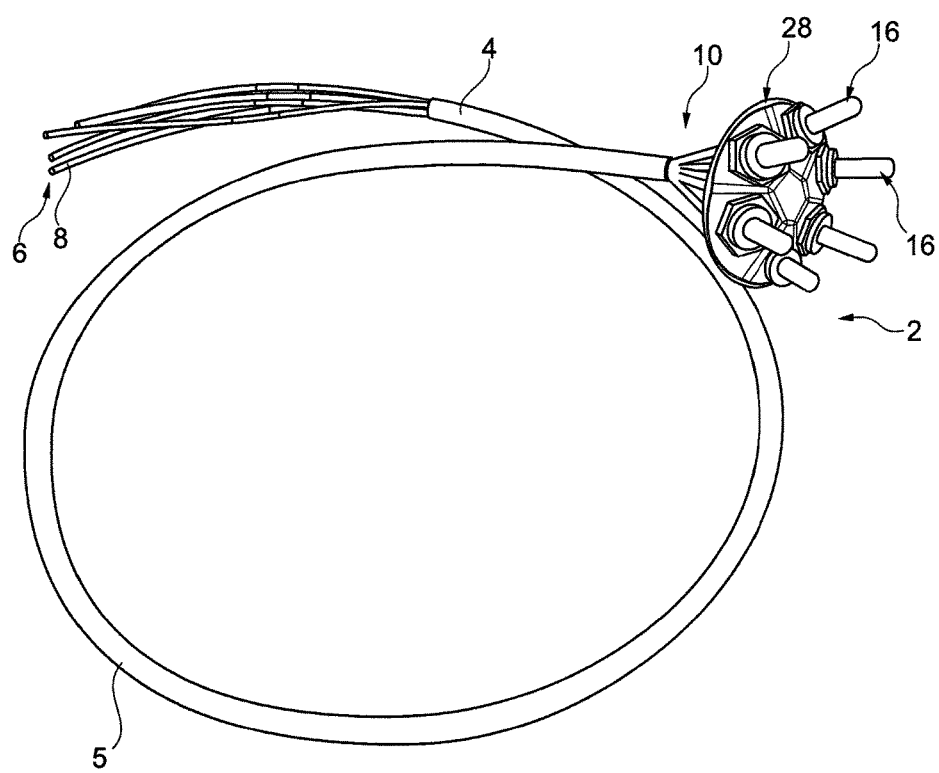
FIG. 5 is perspective view of the endoscopy monitoring apparatus.

Referring to the figures, there is shown endoscopy monitoring apparatus 2 for monitoring the efficacy of an endoscopy cleaning process according to an embodiment of the present invention. The apparatus 2 comprises six elongate and substantially flexible lumen devices 4. Each lumen device 4 has a relatively fine channel defined therein to replicate a difficult cleaning challenge that may be faced with some endoscopy apparatus. For example, in the illustrated example, three lumen devices are provided with a 1 mm diameter channel and three lumen devices are provided with a 2 mm diameter channel. The lumen devices can be colour coded to allow a user to easily visualise the channel diameter of each device. It is to be noted that the lumen devices could have any suitable diameter channel defined therein as required. The lumen devices 4 are typically joined together for neatness using one or more connection means, such as a cable tie and/or outer sleeve 5. The joining means are typically separate to, independent of and/or a spaced distance apart from a holder device 28.

A first end 6 of each lumen device 4 has a connection 8 with an opening defined therein to allow cleaning fluid to pass therethrough and into the channel of device 4 during a cleaning process. A second end 10 of each lumen device 4 has attachment means in the form of a screw thread connection 12. An opening 14 is defined through the screw thread connection 12 to allow fluid communication with the channel of the device.

An indicator holding device 16 is provided for attachment to the second end 10 of lumen device 4. Indicator device 16 has a first end 18 provided with a screw thread connection 20 that is substantially complementary to screw thread connection 12 of lumen device 4, thereby allowing detachable connection with the same in use. A nut 22 is provided with an internal screw thread substantially complementary to the screw thread 20 of indicator device 16, thereby allowing engagement therewith in use.

A second end 24 of the indicator device has an indicator holding element in the form of a blind end channel 26 for the location of a soil test strip therein in use. The soil test strip typically contains a soil test thereon which is washed off if the cleaning process has been successful. The channel 26 is substantially transparent so a user can easily view the test soil strip when it is located in the channel in use.

According to one aspect of the present invention there is provided a holder device 28 for maintaining the position of the indicator holding devices 16 together and in a required orientation. The holder device 28 consists of a body portion having a top surface 30 and a base surface 32. The top surface 30 is substantially dome shaped or has a narrowing taper from a base edge 34 to a top edge 36, such that at least part of the top surface is provided at an acute angle to the base edge or top edge of device 28. In the illustrated example, this angled surface is provided at 21.8 degrees to the base or top edge.

The angled surface is divided into segments 38, with each segment provided in a different orientation or facing a different direction with respect to an adjacent segment or other segment. An aperture 40 is defined in each segment 38 for the location of the screw thread connection of the lumen device 4 and the indicator holding device 16 therethrough. The aperture in each segment is substantially centrally located and each aperture is an equidistance space apart from adjacent apertures. With the indicator holding device and lumen device attached to each aperture of the holder device 28, this maintains each indicator holding device in a different orientation with respect to each other to allow easy visualisation of the indicator holding element 26 by a user viewing the device. In addition, each indicator device is kept together in a neat arrangement and is a spaced distance above or apart from a surface in which the apparatus is to be located in use. The indicator holding device protrudes outwardly, and preferably protrudes outwardly in a substantially linear manner, from the top surface of holder device 28.

The base edge 34 of the holder device 28 has a substantially circular circumference so that it can be placed in any orientation on a surface in use. However, the circumference of the holder device could be any shape as required.

In use, a part of the base edge 34 of the holder device 28 rests on a surface and the remaining part of the base edge is a spaced distance above the surface. The orientation of the holder device can be changed simply by moving the part of the base edge in contact with the surface.

Although the holder device is shown with 6 apertures defined therein for the attachment of 6 indicator devices and 6 lumen devices, it will be appreciated that any number of apertures could be provided for the attachment of a corresponding or less number of indicator devices and/or lumen devices thereto in use.

The invention claimed is:

1. An endoscope monitoring apparatus holder device of an endoscope monitoring apparatus, the endoscope monitoring apparatus being configured to monitor efficacy of an endoscope cleaning process, said endoscope monitoring apparatus holder device comprising:
    a body portion with two or more apertures defined in said body portion, said apertures being a spaced distance apart from one another, each of said apertures being defined such that a part of the endoscope monitoring apparatus attached to the aperture is connected to one of a plurality of indicator holding devices attached to the aperture, the part of the endoscope monitoring apparatus being connected to the one indicator holding device through the aperture, the body portion comprising an top surface and a base surface, the one indicator holding device being maintained on the body portion to protrude outwardly from the top surface, the top surface having a top edge at an inner portion of the top surface and a base edge at an outer portion of the top surface, the apertures being defined in a narrowing taper of said top surface that extends between said top edge of said top surface and said base edge of said top surface.

2. An endoscope monitoring apparatus holder device according to claim 1, wherein at least part of the top surface is provided at an acute angle with respect to the top edge of the top surface.

3. An endoscope monitoring apparatus holder device according to claim 2, wherein the acute angle of the top surface with respect to the top edge is substantially less than 90 degrees.

4. An endoscope monitoring apparatus holder device according to claim 3, wherein the acute angle is less than or equal to 45 degrees.

5. An endoscope monitoring apparatus holder device according to claim 3, wherein the acute angle is between 15-25 degrees.

6. An endoscope monitoring apparatus holder device according to claim 3, wherein the acute angle is 21 degrees+/−1 degree.

7. An endoscope monitoring apparatus holder device according to claim 3, wherein the two or more apertures are defined in the top surface, and
    wherein the acute angle is configured to enable the indicator holding devices and the endoscopy monitoring apparatus to be positioned within the apertures at one or more of a plurality of angles and a plurality of orientations with respect to each other.

8. An endoscope monitoring apparatus holder device according to claim 1, wherein at least part of the top surface is provided at an acute angle with respect to the base edge of the top surface.

9. An endoscope monitoring apparatus holder device according to claim 1, wherein the narrowing taper is at least one of an angled surface, a curved surface, a convexed surface, and a domed surface.

10. An endoscope monitoring apparatus holder device according to claim 1, wherein the top surface of the body portion is divided into a plurality of segments, each of the segments being provided in a non-linear arrangement, in a non-planar arrangement, at a different angle, and/or at a different orientation to an adjacent one of the segments or another one of the segments.

11. An endoscope monitoring apparatus holder device according to claim 10, wherein the top surface of the body portion is divided into six segments.

12. An endoscope monitoring apparatus holder device according to claim 10 or 11, wherein said apertures are respectively defined in two or more of the segments.

13. An endoscope monitoring apparatus holder device according to claim 1, wherein one of the base edge of the body portion and the top surface of the body portion are substantially circular in shape.

14. An endoscope monitoring apparatus holder device according to claim 1, wherein one of the base edge of the body portion and the top surface of the body portion is one of substantially square, rectangular, triangular, pentagonal, octagonal, and hexagonal in shape.

15. An endoscope monitoring apparatus holder device according to claim 1, wherein the top surface of the body portion is substantially symmetrical in shape.

16. An endoscope monitoring apparatus holder device according to claim 1, wherein the top surface of the body portion is substantially asymmetrical in shape.

17. An endoscope monitoring apparatus holder device according to claim 1, wherein the base surface of the body portion is one or more of partially recessed, concave, curved, and angled in shape.

18. An endoscope monitoring apparatus holder device according to claim 1, wherein the base surface of the body portion is one of substantially linear, planar, and solid in form.

19. An endoscope monitoring apparatus holder device according to claim 1, wherein two or more elongate lumen devices of the endoscope monitoring apparatus are at least one of provided, integrally formed, and associated with the body portion.

20. An endoscope monitoring apparatus holder device according to claim 19, wherein the two or more elongate lumen devices are substantially flexible in form.

21. An endoscope monitoring apparatus holder device according to claim 20, wherein a first end of a plurality of the elongate lumen devices has an opening through which cleaning fluid passes.

22. An endoscope monitoring apparatus holder device according to claim 20, wherein a second end of a plurality of the elongate lumen devices is one of:

provided, integral, or associated with the indicator holding devices that respectively correspond with the elongate lumen devices; and provided or associated with attachment means configured to allow attachment of the elongate lumen device with the indicator holding devices respectively corresponding therewith.

23. An endoscope monitoring apparatus holder device according to claim 22, wherein the attachment means is associated with one or more of the elongate lumen devices and the indicator holding devices, the attachment means comprising one or more of a plurality of screw threads, a plurality of nuts, a plurality of bolts, a plurality of inter-engaging members, a plurality of detachable attachment means, and a plurality of friction fits.

24. An endoscope monitoring apparatus holder device according to claim 19, wherein a channel is defined through each of the elongate lumen devices to correspond with a respective endoscopy apparatus.

25. An endoscope monitoring apparatus holder device according to claim 24, wherein the diameter of the channel is in a range from about 1 mm to about 2 mm.

26. An endoscope monitoring apparatus holder device according to claim 19, wherein a second end of each of the elongate lumen devices is provided with threaded attachment means provided in a corresponding one of the apertures in the holding device, and wherein an attachment nut is joined to the threaded attachment means via the top surface of the body portion to retain the elongated lumen device with respect to the body portion.

27. An endoscope monitoring apparatus holder device according to claim 1, wherein each of the indicator holding devices is respectively dimensioned to allow indicator means to be located therein.

28. An endoscope monitoring apparatus holder device according to claim 27, wherein the indicator means is one or more of:

arranged to allow an assessment of the endoscope cleaning process in which the body portion is used to occur; and a test soil strip or device.

29. An endoscope monitoring apparatus holder device according to claim 1, wherein the indicator holding devices are formed from substantially transparent material.

30. An endoscope monitoring apparatus holder device according to claim 1, wherein at least part of the one indicator holding device protrudes outwardly from the top surface of the body portion.

31. An endoscope monitoring apparatus holder device according to claim 1, wherein the one indicator holding device is substantially rigid in form.

32. An endoscope monitoring apparatus, comprising:

an endoscope monitoring apparatus holder device according to claim 1; and two or more elongate lumen devices that are at least one of provided, integrally formed, and associated with the body portion of the endoscope monitoring apparatus holder device.

* * * * *